United States Patent
Lau et al.

(10) Patent No.: US 7,918,807 B2
(45) Date of Patent: Apr. 5, 2011

(54) SYSTEM, METHOD AND COMPUTER INSTRUCTIONS FOR ASSESSING ALERTNESS OF AN OPERATOR OF AN IMAGE REVIEW SYSTEM

(75) Inventors: Denny W. Lau, Sunnyvale, CA (US); Vijaykalyan Yeluri, Sunnyvale, CA (US)

(73) Assignee: General Electric Company, Schenectady, NY (US)

( * ) Notice: Subject to any disclaimer, the term of this patent is extended or adjusted under 35 U.S.C. 154(b) by 1261 days.

(21) Appl. No.: 11/205,449

(22) Filed: Aug. 17, 2005

(65) Prior Publication Data

US 2007/0040691 A1    Feb. 22, 2007

(51) Int. Cl.
*A61B 5/103* (2006.01)
*A61B 5/117* (2006.01)
*A61B 13/00* (2006.01)

(52) U.S. Cl. .................. 600/587; 600/558; 600/595

(58) Field of Classification Search .................. 600/300, 600/372, 382, 383, 544, 545, 546, 547, 558, 600/559, 587, 595; 128/920, 922; 340/500, 340/573.1, 575, 576; 382/100, 110, 128; 702/1, 19, 150, 152, 153, 189
See application file for complete search history.

(56) References Cited

U.S. PATENT DOCUMENTS

| | | | | |
|---|---|---|---|---|
| 5,311,877 A * | 5/1994 | Kishi | ............................ | 600/545 |
| 5,433,223 A * | 7/1995 | Moore-Ede et al. | .......... | 128/898 |
| 5,583,590 A * | 12/1996 | Clupper | ........................ | 351/200 |
| 5,649,061 A * | 7/1997 | Smyth | .............................. | 706/16 |
| 5,689,241 A * | 11/1997 | Clarke et al. | .................. | 340/575 |
| 5,813,993 A * | 9/1998 | Kaplan et al. | .................. | 600/544 |
| 5,835,008 A * | 11/1998 | Colemere, Jr. | ................ | 340/439 |
| 5,884,626 A * | 3/1999 | Kuroda et al. | ................ | 600/300 |
| 6,070,098 A * | 5/2000 | Moore-Ede et al. | .......... | 600/544 |
| 6,097,295 A * | 8/2000 | Griesinger et al. | ........... | 340/576 |
| 6,129,681 A * | 10/2000 | Kuroda et al. | ................ | 600/544 |
| 6,346,887 B1 * | 2/2002 | Van Orden et al. | ........... | 340/575 |
| 6,496,724 B1 * | 12/2002 | Levendowski et al. | ....... | 600/544 |
| 6,661,345 B1 * | 12/2003 | Bevan et al. | .................. | 340/575 |
| 6,927,694 B1 * | 8/2005 | Smith et al. | ................... | 340/576 |
| 7,435,227 B2 * | 10/2008 | Farbos | .......................... | 600/558 |

* cited by examiner

*Primary Examiner* — Jeffrey G Hoekstra
(74) *Attorney, Agent, or Firm* — McAndrews, Held & Malloy, Ltd.; Michael A. Dellapenna

(57) ABSTRACT

Certain embodiments of the present invention provide a system, method and computer instructions for assessing alertness of an operator of an image review system. In an embodiment, such a system includes: an input module configured to allow alertness data to be input; an alertness assessment module configured to evaluate alertness based on the alertness data; and an output module configured to output information based on the evaluation made by the alertness assessment module. In certain embodiments, the input module may input alertness data from: a three-dimensional coordinate tracking system; a brain wave monitoring device; an eye movement monitoring device; a video recording device; and/or an eye closure monitoring device, for example. In certain embodiments, the alertness assessment module may evaluate alertness data using: a Psychomotor Vigilance Performance Task; the Karolinska Sleepiness Scale; and/or a Visual Analogue Sleepiness Scale, for example.

21 Claims, 2 Drawing Sheets

SYSTEM, METHOD AND COMPUTER INSTRUCTIONS FOR ASSESSING ALERTNESS OF AN OPERATOR OF AN IMAGE REVIEW SYSTEM

BACKGROUND OF THE INVENTION

The present invention generally relates to a system, method and computer instructions for assessing alertness of an operator of an image review system. More particularly, the present invention relates to a system, method and computer instructions for inputting alertness data; evaluating alertness based on the alertness data; and outputting information based on the evaluation.

Imaging technology is used in medicine to aid diagnosis of ailments. Image review systems, such as Picture Arching and Communicating System (PACS) workstations, display images for that purpose. Operator's of image review stations, such as radiologists, may review many images in connection with making a single diagnosis.

In making a diagnosis, quality assurance is of utmost importance. Certain measures are currently taken to ensure that each diagnosis is based on complete and correct information. For example, images are previewed by technologists to ensure that the images were acquired properly. Further, information systems that store and display images contain integrity checks to ensure that the images and other data have not been altered. Finally, image display devices are calibrated regularly to ensure that display quality meets certain standards.

However, there is currently no system that performs a quality assurance check on the operator of an image review system. Operators of image review systems work in shifts and, in emergency situations, can be requested to view images and make diagnoses at anytime. Working long hours or during abnormal hours can cause fatigue, sleep loss and circadian disruption, which may lead to a decrease in alertness and performance. Without a quality assurance system monitoring the operator of an image review system, performance quality may be sub-standard without being detected. As a result, the quality of healthcare may be degraded and patients may suffer.

Thus, there is a need for a system, method and computer instructions for assessing alertness of an operator of an image review system.

BRIEF SUMMARY OF THE INVENTION

Certain embodiments of the present invention provide a system, method and computer instructions for assessing alertness of an operator of an image review system. In an embodiment, a system for assessing alertness of an operator of an image review system includes: an input module configured to allow alertness data to be input; an alertness assessment module configured to evaluate alertness based on the alertness data; and an output module configured to output information based on the evaluation made by the alertness assessment module. In certain embodiments, the input module may input alertness data from: a three-dimensional coordinate tracking system; a brain wave monitoring device; an eye movement monitoring device; a video recording device; and/or an eye closure monitoring device, for example. In certain embodiments, the alertness assessment module may evaluate alertness data using: a Psychomotor Vigilance Performance Task; the Karolinska Sleepiness Scale; and/or a Visual Analogue Sleepiness Scale, for example.

In an embodiment, a method for assessing alertness of an operator of an image review system includes: inputting alertness data; evaluating alertness based on the alertness data; and outputting information based on the evaluation. In certain embodiments, the alertness data may be input using: a three-dimensional coordinate tracking system; a brain wave monitoring device; an eye movement monitoring device; a video recording device; and/or an eye closure monitoring device. In certain embodiments, the alertness data may be evaluated using: a Psychomotor Vigilance Performance Task; the Karolinska Sleepiness Scale; and/or a Visual Analogue Sleepiness Scale.

In an embodiment, a computer-readable storage medium includes a set of computer instructions for assessing alertness of an operator of an image review system. The set of instructions includes: an input routine that allows alertness data to be input; an alertness assessment routine that evaluates alertness based on the alertness data; and an output routine that outputs information based on the evaluation made by the alertness assessment routine. In certain embodiments, the input routine may allow alertness data to be input from: a three-dimensional coordinate tracking system; a brain wave monitoring device; an eye movement monitoring device; a video recording device; and/or an eye closure monitoring device. In certain embodiments, the alertness assessment routine may evaluate alertness data using: a Psychomotor Vigilance Performance Task; the Karolinska Sleepiness Scale; and/or a Visual Analogue Sleepiness Scale.

Figure 1:
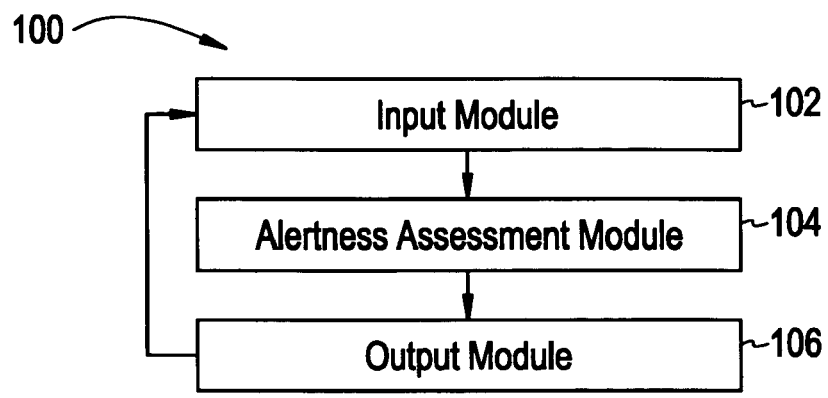
FIG. 1 illustrates a system for assessing alertness of an operator of an image review system used in accordance with an embodiment of the present invention.

The foregoing summary, as well as the following detailed description of embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF CERTAIN EMBODIMENTS

FIG. 1 illustrates a system for assessing alertness of an operator of an image review system used in accordance with an embodiment of the present invention. The system 100 in FIG. 1 includes an input module 102 configured to allow alertness data to be input; an alertness assessment module 104 configured to evaluate alertness based on the alertness data; and an output module 106 configured to output information based on the evaluation made by the alertness assessment module 104.

In the system 100, the input module 102 is configured to allow alertness data to be input. The input module 102 may be configured to allow alertness data to be input in many ways.

Figure 4:
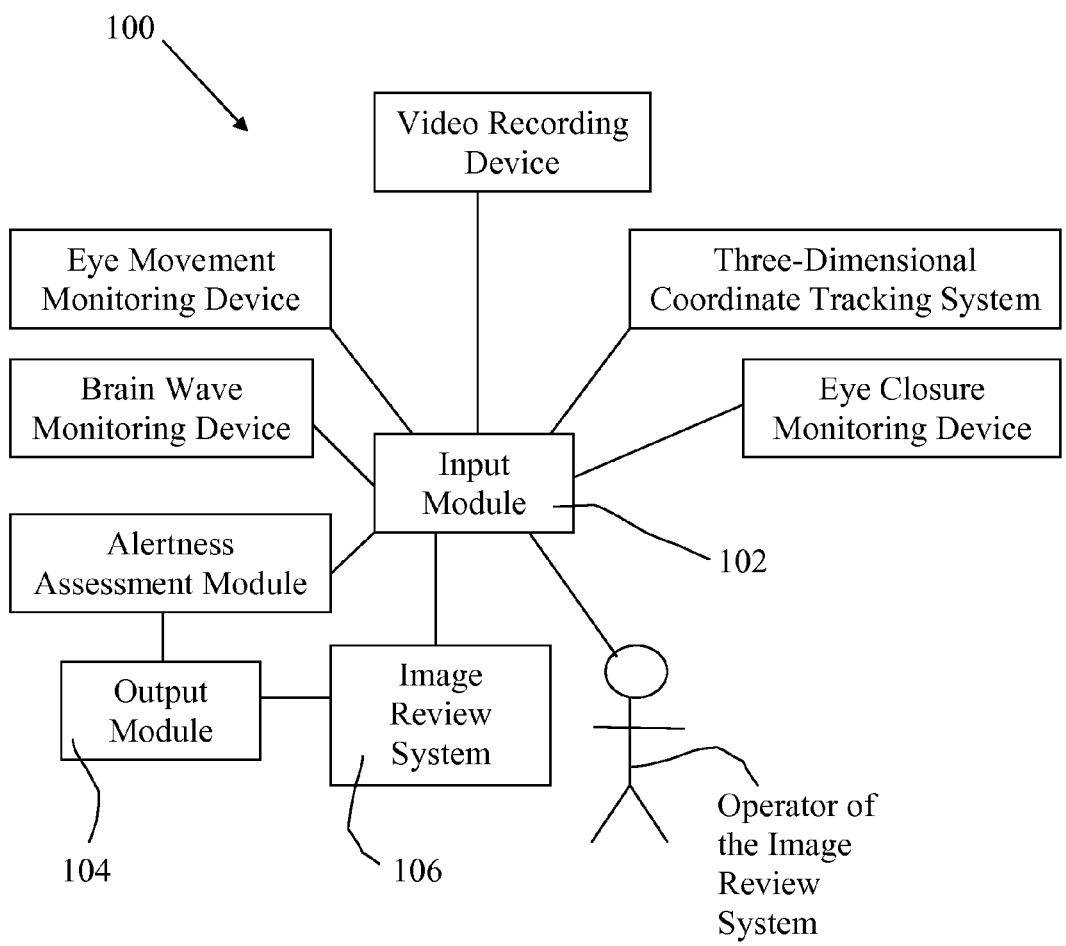
FIG. 4 illustrates a system for assessing alertness of an operator of an image review system used in accordance with an embodiment of the present invention.

For example, the input module 102 may be configured to allow alertness data to be input from a three-dimensional coordinate tracking system (as shown, for example, in FIG. 4), such as a capacitive sensor array for example, that is implemented separately and/or integrated into the input module 102. In such an embodiment, the three-dimensional coordinate tracking system may gather data regarding head movements of an operator of an image review system. The head movement data is a type of alertness data.

In an alternative embodiment, the input module 102 may be configured to allow alertness data to be input from a brain wave monitoring device (as shown, for example, in FIG. 4), such as an electro-encphalograph (EEG) for example, that is implemented separately and/or integrated into the input module 102. In such an embodiment, the brain wave monitoring device may gather data regarding brain wave activity of an operator of an image review system. The brain wave activity data is a type of alertness data.

In an alternative embodiment, the input module 102 may be configured to allow alertness data to be input from an eye movement monitoring device (as shown, for example, in FIG. 4), such as an electro-oculogram (EOG) or an infrared camera with retinal reflectance for example, that is implemented separately and/or integrated into the input module 102. In such an embodiment, the eye movement monitoring device may gather data regarding eye movement of an operator of an image review system. The eye movement data is a type of alertness data. In an embodiment, the eye movement monitoring device may detect whether an operator's eyes are focused on the images that are displayed on the monitor(s) of the image review system as opposed to other objects displayed on the monitor(s), for example. It may be desirable to configure the eye movement monitoring device to gather data regarding eye movement of an operator of an image review system in other ways, as known to those skilled in the art.

In an alternative embodiment, the input module 102 may be configured to allow alertness data to be input from a video recording device (as shown, for example, in FIG. 4) that is implemented separately and/or integrated into the input module 102. In such an embodiment, the video recording device may gather data regarding facial movements of operator of an image review system. The facial movement data is a type of alertness data.

In an alternative embodiment, the input module 102 may be configured to allow alertness data to be input from an eye closure monitoring device (as shown, for example, in FIG. 4), such as those used in connection with driver fatigue monitors for example, that is implemented separately and/or integrated into the input module 102. In such an embodiment, the eye closure monitoring device may gather data regarding eye closures of an operator of an image review system. The eye closure data is a type of alertness data.

It may be desirable to configure the input module 102 to allow other types of alertness data to be input in other ways, as known to those skilled in the art.

In the system 100, the alertness assessment module 104 is configured to evaluate alertness based on alertness data input from the input module 102. The alertness assessment module 104 may be configured to evaluate many types of alertness data. For example, the alertness assessment module 104 may be configured to evaluate alertness based on: head movement data; brain wave activity data; eye movement data; facial movement data; and/or eye closure data. It may be desirable to configure the alertness assessment module 104 to evaluate other types of alertness data, as known to those skilled in the art.

The alertness assessment module 104 may be configured to evaluate alertness data using many scales. For example, the alertness assessment module 104 may be configured to evaluate alertness data using: a Psychomotor Vigilance Performance Task; the Karolinska Sleepiness Scale, which assigns a numerical value to levels of sleepiness (1=extremely alert, 5=neither alert nor sleepy, and 9=extremely sleepy); a Visual Analogue Sleepiness Scale; and/or any acceptable scale that may be used in connection with evaluating head movement data, brain wave activity data, eye movement data, facial movement data and/or eye closure data. It may be desirable to configure the alertness assessment module 104 to evaluate alertness data using other scales, as known to those skilled in the art.

The alertness assessment module 104 may be configured to evaluate alertness data in many ways. For example, if alertness data is taken at multiple times during the viewing of a single image, the alertness assessment module 104 may be configured to evaluate only the last set of alertness data. This may aid in detection of situations where an operator of an image review system is alert when the operator begins viewing an image, but is no longer alert when the operator finishes viewing the image. In an alternative embodiment, the alertness assessment module 104 may be configured to evaluate all of the alertness data gathered during the viewing of a single image and then only retain the alertness data that tends to show that an operator of an image review system was not sufficiently alert. This may aid in detection of situations where an operator of an image review system is alert at some point while reviewing an image, but not the entire time the image is being viewed. It may be desirable to configure the alertness assessment module 104 to evaluate alertness data in other ways, as known to those skilled in the art.

The alertness assessment module 104 may be configured to evaluate alertness data at different times. For example, the alertness assessment module 104 may be configured to evaluate alertness data after a single image is reviewed, after an exam containing more than one image is reviewed; and/or at any interval in between.

In the system 100, the output module 106 is configured to output information based on the evaluation made by the alertness assessment module 104. The output module 106 may be configured to output information at different times. For example, the output module 106 may be configured to output information after a single image is reviewed, after an exam containing more than one image is reviewed; and/or at any interval in between.

The output module 106 may be configured to output many types of information. For example, the output module 106 may be configured to output a warning(s) indicating that an operator of an image review system was not sufficiently alert when viewing a certain image(s). The output module 106 may also be configured to output a notification that an operator of an image review system was sufficiently alert when viewing all images, for example. The output module 106 may also be configured to output nothing when an operator of an image review system was sufficiently alert when viewing all images, for example. It may be desirable to configure the output module 106 to output other types of information, as known to those skilled in the art.

The output module 106 may be configured to output information in many ways. For example, the output module 106 may be configured to output information as a visual display, an audio display, printed matter, a facsimile transmission, and/or electronic mail. It may be desirable to configure the output module 106 to output information in other ways, as known to those skilled in the art.

The output module 106 may be configured to allow an operator of an image review system to choose whether or not the image review system should redisplay an image(s) associated with alertness data that indicates the operator was not sufficiently alert when viewing the image(s). The output module 106 may also be configured to require an image review system to redisplay an image(s) associated with alertness data that indicates the operator of the image review system was not sufficiently alert when viewing the image(s).

The modules of the system 100 may be implemented in many ways. For example, the modules may be implemented in hardware and/or software. The modules may be implemented separately and/or integrated in various combinations. It may be desirable to implement the modules of the system 100 in other ways, as known to those skilled in the art.

The system 100 may also be implemented in many ways. For example, the system 100 may be integrated with previously installed software applications as an add-on product. The system 100 may be integrated with systems and workstations connected to a Hospital Information System (HIS) and/or a Radiology Information System (RIS), such as an Ultrasound imaging workstation, a Computed Tomography (CT) imaging system, a Magnetic Resonance (MR) imaging system, and/or a Picture Arching and Communicating System (PACS), for example. It may be desirable to implement the system 100 in other ways on other types of systems and/or workstations, as known to those skilled in the art.

In operation, the system 100 may be implemented in connection with a PACS workstation. In such an embodiment, the input module 102 may be configured so that data may be input from an eye closure monitoring device that is integrated into the PACS workstation. The eye closure monitoring device may generate alertness data based on the eye closures of an operator of the PACS workstation while the operator views images displayed on the PACS workstation. The alertness data may be passed to the alertness assessment module 104 when all images have been viewed by the operator of the PACS workstation. The alertness assessment module 104 may then evaluate the alertness data to determine if the operator of the PACS workstation was sufficiently alert while viewing each image. If there is alertness data indicating that the operator of the PACS workstation was not sufficiently alert when viewing an image(s), the alertness assessment module 104 may pass that information to the output module 106. The output module 106 may then warn the operator of the PACS workstation that the operator was not sufficiently alert when viewing a certain image(s) by displaying a warning message on the screen of the PACS workstation. The output module 106 may also allow the operator to view that image(s) again by displaying such an option on the screen of the PACS workstation. If the operator chooses to view that image(s) again, the image(s) is redisplayed and the process starts again. If the operator chooses not to view the image(s) again, the image(s) is not redisplayed and the process is finished.

Figure 2:
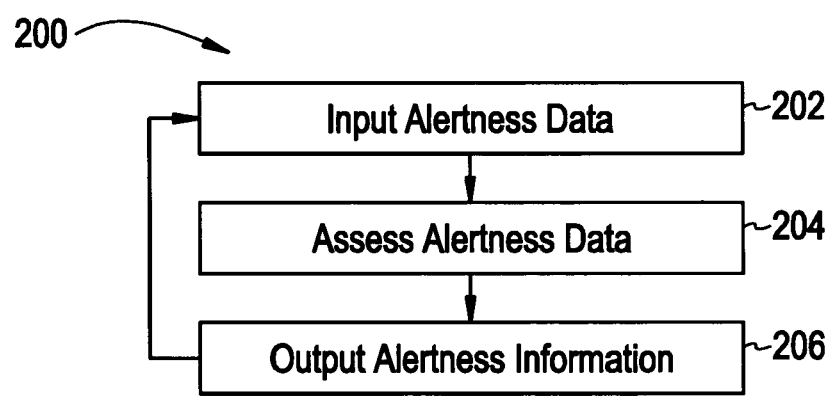
FIG. 2 illustrates a method for assessing alertness of an operator of an image review system used in accordance with an embodiment of the present invention.

FIG. 2 illustrates a method for assessing alertness of an operator of an image review system used in accordance with an embodiment of the present invention. At 202, alertness data is input. For example, alertness data may be input from an eye closure monitoring device that is integrated into a PACS workstation. The eye closure monitoring device may generate alertness data based on the eye closures of an operator of the PACS workstation while the operator views images displayed on the PACS workstation. At 204, alertness data is assessed. For example, alertness data may be evaluated to determine if the operator of the PACS workstation was sufficiently alert while viewing each image. At 206, alertness information is output. For example, if there is alertness data indicating that the operator of the PACS workstation was not sufficiently alert when viewing an image(s), the operator of the PACS workstation may be warned that the operator was not sufficiently alert when viewing a certain image(s). The operator of the PACS workstation may then choose to view that image(s) again. If the operator chooses to view that image(s) again, the image(s) is redisplayed and the process starts again. If the operator chooses not to view that image(s) again, the image(s) is not redisplayed and the process is finished.

Due to long and/or abnormal working hours, operators of image review systems may be fatigued and thus may commit mistakes when reviewing images. Applying the method 200, as described above and/or in light of the description of FIG. 1, may provide assurance that operators of image review systems are sufficiently alert when reviewing images, which may prevent misdiagnosis and increase operator confidence.

Figure 3:
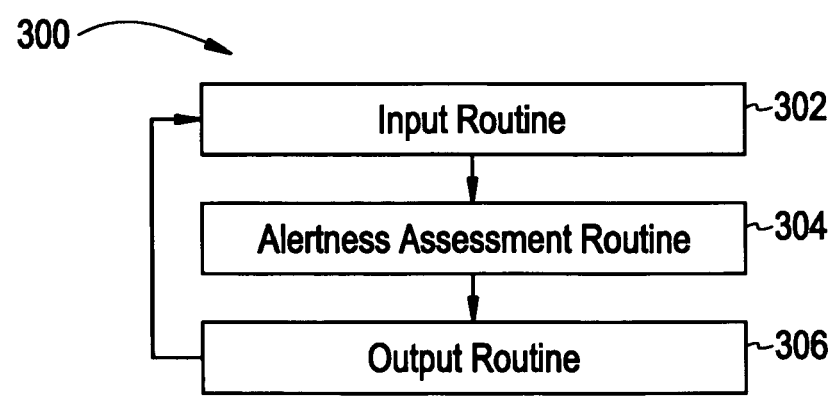
FIG. 3 illustrates a set of computer instructions for assessing alertness of an operator of an image review system used in accordance with an embodiment of the present invention.

FIG. 3 illustrates a set of computer instructions 300 for assessing alertness of an operator of an image review system used in accordance with an embodiment of the present invention. The set of computer instructions 300 in FIG. 3 includes an input routine 302, which allows alertness data to be input, an alertness assessment routine 304, which evaluates alertness based on the alertness data, and an output routine 306, which outputs information based on the evaluation made by the alertness assessment routine.

In an embodiment, the input routine 302, the alertness assessment routine 304 and the output routine 306 may be implemented and/or may perform functions similar to the input module 102, the alertness assessment module 104 and the output module 106, respectively, as described above in relation to FIG. 1.

While the invention has been described with reference to embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A system comprising:
a diagnostic image review system configured to display a plurality of images such that each displayed image can be reviewed by an operator for diagnostic purposes;
an input module operably connected to the diagnostic image review system, the input module configured to input alertness data regarding alertness of the operator while the operator reviews each displayed image, the input module and diagnostic image review system configured such that each of the displayed images is associated with alertness data that was input while the image was being displayed by the diagnostic image review system;
an alertness assessment module operably connected to the input module and configured to evaluate said alertness data to identify one or more images that were displayed by the diagnostic image review system while the operator was not sufficiently alert; and
an output module operably connected to the alertness assessment module and configured to output information based on the evaluation made by the alertness assessment module.

2. The system of claim 1, wherein said input module is configured to input data from a three-dimensional coordinate tracking system.

3. The system of claim 1, wherein said input module is configured to input data from at least one of: a brain wave monitoring device, and an eye movement monitoring device.

4. The system of claim 1, wherein said input module is configured to input data from a video recording device.

5. The system of claim 1, wherein said input module is configured to input data from an eye closure monitoring device.

6. The system of claim 1, wherein said alertness assessment module evaluates alertness data using at least one of: a psychomotor vigilance performance task; the Karolinska sleepiness scale; and a visual analogue sleepiness scale.

7. The system of claim 1, wherein said diagnostic image review system is a picture arching and communicating system workstation.

8. A system comprising:
a diagnostic image review system configured to display a plurality of images such that each displayed image can be reviewed by an operator for diagnostic purposes;
an input module operably connected to the diagnostic image review system, the input module configured to input alertness data regarding alertness of the operator while the operator reviews each displayed image, the input module and diagnostic image review system configured such that each of the displayed images is associated with alertness data that was input while the image was being displayed by the diagnostic image review system;
an alertness assessment module operably connected to the input module and configured to evaluate said alertness data to identify one or more images that were displayed by the diagnostic image review system while the operator was not sufficiently alert, wherein the alertness assessment module is configured to receive alertness data multiple times during the display of each image, and wherein the alertness assessment module is configured to indicate that the operator of the image review system was not sufficiently alert when reviewing a displayed image if any of the alertness data associated with the displayed image indicates that the operator was not sufficiently alert when reviewing the displayed image; and
an output module operably connected to the alertness assessment module and configured to output information based on the evaluation made by the alertness assessment module.

9. The system of claim 8, wherein said input module is configured to input data from a three-dimensional coordinate tracking system.

10. The system of claim 8, wherein said input module is configured to input data from at least one of: a brain wave monitoring device, and an eye movement monitoring device.

11. The system of claim 8, wherein said input module is configured to input data from a video recording device.

12. The system of claim 8, wherein said input module is configured to input data from an eye closure monitoring device.

13. The system of claim 8, wherein said alertness assessment module evaluates alertness data using at least one of: a psychomotor vigilance performance task; the Karolinska sleepiness scale; and a visual analogue sleepiness scale.

14. The system of claim 8, wherein said diagnostic image review system is a picture arching and communicating system workstation.

15. A system comprising:
a diagnostic image review system configured to display a plurality of images such that each displayed image can be reviewed by an operator for diagnostic purposes;
an input module operably connected to the diagnostic image review system, the input module configured to input alertness data regarding alertness of the operator while the operator reviews each displayed image, the input module and diagnostic image review system configured such that each of the displayed images is associated with alertness data that was input while the image was being displayed by the diagnostic image review system;
an alertness assessment module operably connected to the input module and configured to evaluate said alertness data to identify one or more images that were displayed by the diagnostic image review system while the operator was not sufficiently alert; and
an output module operably connected to the alertness assessment module and configured to output information based on the evaluation made by the alertness assessment module, wherein the output module is configured to output an image identified by the alertness assessment module as being displayed by the diagnostic image review system while the operator was not sufficiently alert such that the output image is redisplayed by the diagnostic image review system.

16. The system of claim 15, wherein said input module is configured to input data from a three-dimensional coordinate tracking system.

17. The system of claim 15, wherein said input module is configured to input data from at least one of: a brain wave monitoring device, and an eye movement monitoring device.

18. The system of claim 15, wherein said input module is configured to input data from a video recording device.

19. The system of claim 15, wherein said input module is configured to input data from an eye closure monitoring device.

20. The system of claim 15, wherein said alertness assessment module evaluates alertness data using at least one of: a psychomotor vigilance performance task; the Karolinska sleepiness scale; and a visual analogue sleepiness scale.

21. The system of claim 15, wherein said diagnostic image review system is a picture arching and communicating system workstation.

* * * * *